United States Patent [19]
Takle et al.

[11] Patent Number: 5,891,689
[45] Date of Patent: Apr. 6, 1999

[54] HEME-BEARING MICROPARTICLES FOR TARGETED DELIVERY OF DRUGS

[75] Inventors: Garry B. Takle; Shaji T. George, both of New York, N.Y.

[73] Assignee: Innovir Laboratories, Inc., New York, N.Y.

[21] Appl. No.: 226,548

[22] Filed: Apr. 12, 1994

[51] Int. Cl.$^6$ .......................... A61K 47/48; A61K 48/00; C12N 15/00; C12N 15/79

[52] U.S. Cl. .................... 435/172.3; 435/174; 935/22; 935/52; 514/44

[58] Field of Search .............................. 435/172.3, 69.1, 435/174; 504/44; 424/450; 935/34, 22, 52; 536/23.1, 24.1

[56] References Cited

U.S. PATENT DOCUMENTS

| | | | |
|---|---|---|---|
| 4,104,466 | 8/1978 | Tsuchida et al. | 562/2 |
| 4,981,957 | 1/1991 | Lebleu et al. | 536/25.2 |
| 5,166,320 | 11/1992 | Wu et al. | 530/395 |
| 5,225,337 | 7/1993 | Robertson et al. | 435/91.31 |

FOREIGN PATENT DOCUMENTS 2 146 525   4/1985   United Kingdom .

OTHER PUBLICATIONS

Majuri et al., 1989. Eur. J. Haematol. 43:220–225, Sep. 1989.

The Merck Index, Tenth Ed., Merck and Co., Inc. 1983, p. 4527.

Aft, R.L., et al., "Hemin–Mediated DNA Strand Scission", *J. Biol. Chem.*, 258(19):12069–12072 (1993).

Cannon, J.B., et al., "Kinetics of the Interaction of Hemin Liposomes with Heme Binding Proteins", *Biochemistry*, 23(16):3715–3721 (1984).

Carvlin, M.J., et al., "Intercalative and Nonintercalative Binding of Large Cationic Porphyrin Ligands to Calf Thymus DNA", *Nucleic Acids Res.*, 11:6121–6139 (1983).

Chowdhury, N.R., et al., "Fate of DNA Targeted to the Liver by Asialoglycoprotein Receptor–Mediated Endocytosis in Vivo", *J. Biol. Chem.*, 268:11265–11271 (1993).

Clarenc, J.P., et al., "Delivery of Antisense Oligonucleotides by Poly(L–lysine) Conjugation and Liposome Encapsulation", *Anti–Cancer Drug Design*, 8(1):81–94 (1993).

Felgner, P.L., et al., "Cationic Lipsosome–Mediated Transfection", *Nature*, 337:387–388 (1989).

Felgner, P.L., "Particulate Systems and Polymers for In Vitro and In Vivo Delivery of Polynucleotides", *Advanced Drug Delivery Reviews*, 5:163–187 (1990).

Felgner, P.L., et al., "Lipofection: A Highly Efficient, Lipid–Mediated DNA–Transfection Procedure", *Proc. Natl. Acad. Sci. USA* 84:7413–7417 (1987).

Fuhrhop, et al., In: *Porphyrins and Metalloporphyrins*, (K.M. Smith, Ed.) (Elsevier, Amsterdam, 804–807 (1975).

Galbraith, R.A., "Heme Binding to Hep G2 Human Hepatoma Cells", *J. Hepatol.*, 10(1):305–310 (1990).

Galbraith, R.A., et al., "Heme Binding to Murine Erythroleukemia Cells", *J. Biol. Chem.*, 260(22):12198–12202 (1985).

Kim, S., et al., "Preparation of Multivesicular Liposomes", *Biochimica et Biophysica Acta*, 728:339–348 (1983).

Larock, "Comprehensive Organic Transformations", VCH, New York, 966–972 (1989).

(List continued on next page.)

*Primary Examiner*—Brian R. Stanton
*Attorney, Agent, or Firm*—Arnall Golden & Gregory, LLP

[57] ABSTRACT

Methods and compositions are described for the directed delivery of ribozymes or other compounds to specific cells which express the heme receptor on their surface using heme-bearing microparticles. Such microparticles are useful in the directed delivery and accumulation of drugs designed to treat hepatic diseases such as viral hepatitis or hepatoma.

26 Claims, 2 Drawing Sheets

OTHER PUBLICATIONS

Lee, K–D., et al., "Recognition of Liposomes by Cells: In Vitro Binding and Endocytosis Mediated by Specific Lipid Headgroups and Surface Charge Density", *Biochimica et Biophysica Acta,* 1103:185–197 (1992).

Leonetti, J–P, et al., "Antibody–targeted Liposomes Containing Oligodeoxyribonucleotides Complementary to Viral RNA Selectively Inhibit Viral Replication", *Proc. Natl. Acad. Sci. USA,* 87(7):2448–2451 (1990).

Leserman, L., et al., "Targeted Liposomes and Intracellular Delivery of Macromolecules", *Horizons in Membrane Biotechnology,* 95–102 (1990).

Liu, D., et al., "Role of Liposome Size and RES Blockade in Controlling Biodistribution and Tumor Uptake of $GM_1$–containing Liposomes", *Biochimica et Biophysica Acta,* 1104(1):95–101 (1992).

Machy, P., et al., "Interferon Sensitive and Insensitive MHC Variants of a Murine Thymoma Differentially Resistant to Methotrexate–Containing Antibody–Directed Liposomes and Immunotoxin", *J. Immunology,* 136(8):3110–3115 (1986).

Machy, P., et al., "Elimination or Rescue of Cells in Culture by Specifically Targeted Liposomes Containing Methotrexate or Formyl–Tetrahydrofolate", *EMBO Journal,* 3(7):1971–1977 (1984).

Milhaud, P.G., et al., "Antibody Targeted Liposomes Containing Poly(rI)•poly(rC) Exert a Specific Antiviral and Toxic Effect on Cells Primed with Interferons α/β or Y", *Biochimica et Biophysica Acta,* 987:15–20 (1989).

Milhaud, P.G., et al., "Free and Liposome–Encapsulated Double–Stranded RNAs as Inducers of Interferon, Interleukin–6, and Cellular Toxicity", *J. of Interferon Res.,* 11(1):261–265 (1991).

Noé, C., et al., "Inhibition of Cell Proliferation with Antibody–Targeted Liposomes Containing Methotrexate–Y–Dimyristoylphosphatidylethanolamine", *Biochimica et Biophysica Acta,* 946:253–260 (1988).

R.R.C. New (ed.) "Liposomes: A Practical Approach", IRL Press, Oxford, 179–180 (1992).

Sells, M.A., et al., "Production of Hepatitis B Virus Particles in Hep G2 Cells Transfected with Cloned Hepatitis B Virus DNA", *Proc. Natl. Acad. Sci. USA,* 84:1005–1009 (1987).

Sinclair, P.R., et al., "Effect of Serum Proteins on Haem Uptake and Metabolism in Primary Cultures of Liver Cells", *Biochem. J.,* 256(19):159–165 (1988).

Smith, A., et al., "Hemopexin–Mediated Heme Uptake by Liver", *J. Biol. Chem.,* 259:12049–12053 (1984).

Suzuki, H., et al., "CD4 and CD7 Molecules as Targets for Drug Delivery from Antibody Bearing Liposomes", *Exp. Cell Res.,* 193(1):112–119 (1991).

Symons, R.H., "Ribozymes", *Critical Reviews in Plant Sciences,* 10(3):189–234 (1991).

Thierry, A.R., et al., "Multidrug Resistance in Chinese Hamster Cells: Effect of Liposome–Encapsulated Doxorubicin", *Cancer Communications,* 1(5):311–316 (1989).

Thierry, A.R., et al., "Overcoming Multidrug Resistance in Human Tumor Cells Using Free and Liposomally Encapsulated Antisense Oligodeoxynucleotides", *Biochem. Biophys. Res. Comm.,* 190(3):952–960 (1993).

Thierry, A.R., et al., "Intracellular Availability of Unmodified, Phosphorothioated and Liposomally Encapsulated Oligodeoxynucleotides for Antisense Activity", *Nuc. Ac. Res.,* 20(21):5691–5698 (1992).

Tipping, E., et al., "Interactions of Small Molecules with Phospholipid Bilayers", *Biochem. J.,* 180:327–337 (1979).

Truneh, A., et al., "A Calmodulin Antagonist Increases the Apparent Rate of Endocytosis of Liposomes Bound to MHC Molecules Via Monoclonal Antibodies", *Exp. Cell Res.,* 155:50–63 (1984).

Wang, C.Y., et al., "Highly Efficient DNA Delivery Mediated by pH–Sensitive Immunoliposomes", *Biochem.,* 28:9508–9514 (1989).

Cannon, "Pharmaceutics and Drug Delivery Aspects of Heme and Porphyrin Therapy", *J. of Pharm. Sci.* 83:435–446 (1993).

Pispisa, et al., "Photophysical Behavior of Poly(L–Lysine) Carrying Porphyrin and Naphthyl Chromophores," *Biopolymers* 34:435–442 (1994).

Spaltro, "The Synthesis and Characterization of the Manganese (III) Chloride Protoporphyrin IX–Poly (Alpha–Amino Acid) Conjugates," *Dissertation Abstracts International* 49–07:2678 (1988).

Tsuchida, et al., "Cooperative Reactions of Poly–L–Lysine–Heme Complex with Molecular Oxygen, Carbon Monoxide, or Cyanide Ion," *Biochim. et Biophysica Acta* 427:520–529 (1976).

Ushakova, et al., "Preparation of Liposomal Forms of Hemin Hydrophobic Derivatives", *Bioorg. Khim.,* 15:1128–1132 (1989).

Yamagishi, et al., "Electric Dichroism Studies on Ferriheme– and Ferroheme–Poly(L–lysine) Complexes at pH 9–12," *Biopolymers* 21:89–100 (1982).

HEME-BEARING MICROPARTICLES FOR TARGETED DELIVERY OF DRUGS

BACKGROUND OF THE INVENTION

The present invention relates generally to delivery of oligonucleotides to targeted cell types, and is in particular a means using microparticulates having on their outer surface molecules which are specifically bound and taken up by cells expressing the heme receptor.

Targeted drug delivery is required in a number of situations where the drug may be toxic if administered in a very high dose in order for sufficient doses to reach an intended site, where the drug is very expensive or where the drug is subject to rapid removal or degradation. Drug delivery, and more recently delivery of oligonucleotides and genes, to targeted cells has been modulated by manipulation of carrier, method of manufacture, and attachment of targeting molecules. Although drugs are traditionally encapsulated in tablets or capsules for oral delivery, encapsulation into more sophisticated vehicles is required for targeted delivery and delivery of molecules such as oligonucleotides and genes, which are extremely sensitive to the presence of nucleases in the body.

Reports of delivery of oligonucleotides using liposomes and polymeric vehicles for local release have been made, although no device is publicly available at this time. Liposomes consist basically of a phospholipid bilayer forming a shell around an aqueous core. Advantages include the lipophilicity of the outer layers which "mimic" the outer membrane layers of cells and that they are taken up relatively easily by a variety of cells. Disadvantages include the non-specific nature of delivery. Polymeric vehicles typically consist of microspheres and microcapsules formed of biocompatible polymers, which are either biodegradable (for example, polylactic acid) or non-biodegradable (for example, ethylenevinyl acetate). Some of the advantages of the polymeric devices are ease of manufacture and high loading capacity, range of size from nanometer to micron diameter, as well as controlled release and degradation profile. However, targeting of the polymeric vehicles remains as problematic as with liposomes. Both liposomes and small polymeric vehicles are referred to herein as "microparticles", unless specifically stated otherwise.

Many different systems have been proposed for targeted drug delivery. The most commonly used method has been to covalently attach specific antibodies to the surface of microparticulate carriers. Few systems have been demonstrated to deliver nucleic acids efficiently.

The use of liposomes for delivery of various drugs, including nucleic acid-based therapeutics, has been reported by Thierry, A. T., et al., *Cancer Comm.*, 1, 311–316 (1989); and Thierry, A. T., et al., *Biochem. Biophys. Res. Comm.*, 190, 952–960 (1993). Liposomes are potentially useful because they protect the encapsulated material from degradation by serum enzymes. Also, liposomes offer a distinct benefit to the delivery of drugs to the liver because, depending on their lipid composition and size, up to 70% of liposomes injected intravenously into mice may quickly locate to the liver, as reported by Liu, D., et al., *Biochim. Biophys. Acta*, 1104, 95–101 (1992).

Hepatocytes contain surface receptors for molecules such as asialoglycoprotein or transferrin, and these proteins have been used as the basis for ligand-directed delivery of certain molecules to hepatocytes, described by Chowdhury, N. R., et al., *J. Biol Chem.* 268, 11265–11271 (1993).

Immunoliposomes, i.e., liposomes bearing antibodies to certain target molecules, have also been used to direct drug delivery. However, the coupling of such complex ligands to the, surface of liposomes presents a number of problems, mainly due to the fact that they have a polypeptide or carbohydrate component and therefore contain multiple reactive groups. Attempts to carry out carbodiimide-mediated peptide bond formation between such complex ligand molecules and primary amino groups on the outer surface of liposomes can result in considerable intramolecular coupling and intermolecular coupling between ligand molecules, in addition to the desired intermolecular coupling between liposome and ligand. Furthermore, this coupling is difficult to regulate because it may result in a significant number of undesirable ligand structures, decreasing efficiency of the reaction. Protein ligands are also immunogenic and could therefore either evoke an immune reaction or result in clearance by the immune system of the body.

It is therefore an object of the present invention to provide a means for targeting microparticles for delivery to specific cell types not using antibodies or other proteins.

It is a further object of the present invention to provide compositions for efficient and reliable delivery to specific cell types, especially of nucleic acid-type molecules, such as antisense and ribozymes.

SUMMARY OF THE INVENTION

Efficient methods and compositions are provided for the targeted delivery of effective concentrations of compounds, including nucleic acid molecules and oligonucleotides such as ribozymes and antisense, proteins, carbohydrate, and synthetic organic and inorganic molecules, or combinations thereof, to cells which express the receptor for heme, especially hepatocytes. Heme is intercalated into or covalently conjugated to the outer surface of the microparticles to form heme-bearing microparticles. In a preferred embodiment the microparticles are liposomes and the compound to be delivered is incorporated into or bound to the surface or between lipid bilayers of the heme-bearing microparticles. The microparticles are then administered to a patient in need of treatment with the incorporated compound, for example, someone with liver disease, since hepatocytes are representative of cells binding heme. Cells expressing the receptors for heme bind the heme-bearing microparticles. The lipid composition of the liposomes facilitates uptake by the cells of the incorporated compound.

BRIEF DESCRIPTION OF THE DRAWINGS

(FIG. 4A) or 4° C. (FIG. 4B)

Figure 1:
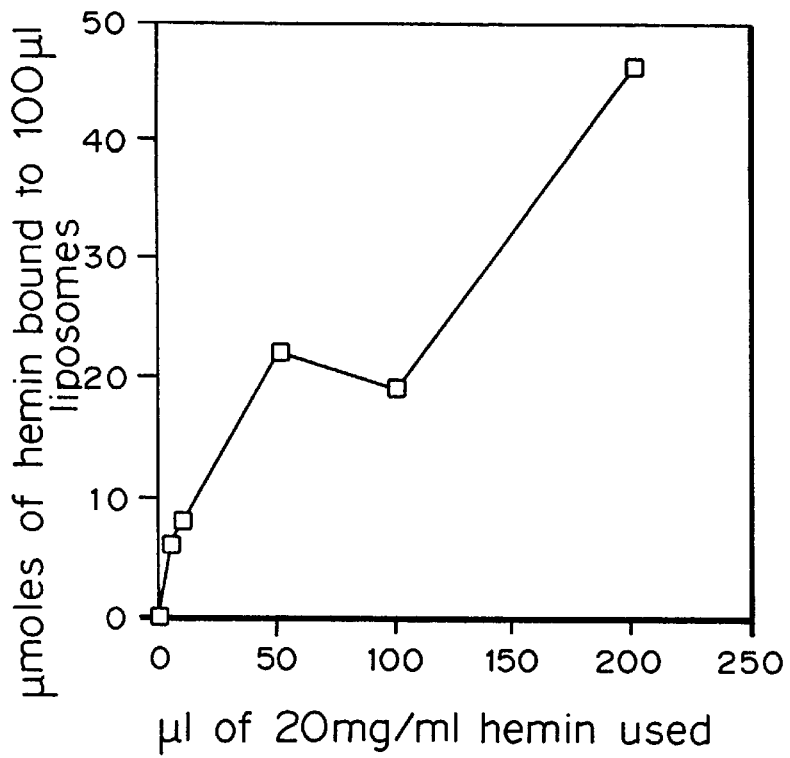
FIG. 1 is a graph of binding of hemin to liposomes formed from a 7:12:5 molar ratio of dimyristoyl phosphatidylglycerol, cholesterol and phosphatidylethanolamine ("DMPG/CH/PE liposomes"), measured as micromoles of hemin bound to 100 microliters liposomes versus microliters of 20 mg hemin/ml, to yield between 50 $\mu$g and 2 mg heme.

versus microliters 10 mg/ml heme in the conjugation reaction. Increasing amounts of heme from zero to two mg were used in the conjugation reaction, and increasing amounts of heme were detected bound to the liposomes.

DETAILED DESCRIPTION OF THE INVENTION

Methods and compositions for the targeted delivery of compounds, including nucleic acid-based therapeutics, other drugs, and non-therapeutic compounds, to specific cells using heme-bearing microparticles are provided. Cells which are targeted for delivery are those expressing the receptor for heme and thereby specifically bind heme-bearing microparticles carrying a compound or combination of compounds. The cells subsequently take up the bound microparticles, and the compounds associated with the microparticles are then released into the cells.

Heme-bearing microparticles offer an advantage in that since they are preferentially bound and taken up by cells that express the heme receptor, such as hepatocytes, the amount of drug or other compound required for an effective dose is significantly reduced. Such targeted delivery may also reduce systemic side effects that can arise from using relatively high drug concentrations in non-targeted delivery methods.

Microparticles

As used herein, microparticles include liposomes, virosomes and micropheres and microcapsules formed of synthetic and natural polymers. In general, the microparticles will have a diameter in the range of nanometers to less than 50 microns, preferably between one and ten microns for administration by injection, most preferably less than five microns for uptake by cells.

Liposomes

Liposomes can be produced by standard methods such as those reported by Kim, et al., *Biochim. Biophys. Acta* 728, 339–348 (1983); Liu, D., et al., *Biochim. Biophys. Acta* 1104, 95–101 (1992); and Lee, et al., *Biochim. Biophys. Acta.*, 1103, 185–197 (1992)), incorporated herein by reference.

Many liposome formulations using many different lipid components have been used in various in vitro cell culture and animal experiments. Parameters have been identified that determine liposomal properties and reported in the literature, for example, by Lee, K. D., et al. *Biochim. Biophys. Acta.*, 1103, 185–197 (1992); Liu, D., Mori, A. and Huang, L., *Biochim. Biophys. Acta*, 1104, 95–101 (1992); Wang, C. Y. and Huang, L., *Biochem.*, 28, 9508–9514 (1989)).

Briefly, the lipids of choice, dissolved in an organic solvent, are mixed and dried onto the bottom of a glass tube under vacuum. The lipid film is rehydrated using an aqueous buffered solution containing the material to be encapsulated by gentle swirling. The hydrated lipid vesicles or liposomes are washed by centrifugation and can be filtered and stored at 4° C. This method is described in more detail in Thierry, A. R. and Dritschilo, A "Intracellular availability of unmodified, phosphorothioated and liposomally encapsulated oligodeoxynucleotides for antisense activity" *Nuc. Ac. Res.* 20:5691–5698 (1992).

Polymeric microparticles

Methods for making polymeric microcapsules and microspheres are known to those skilled in the art and include solvent evaporation, solvent casting, spray drying and solvent extraction. Examples of useful polymers include polysaccharides, polyanhydrides, polyorthoesters, polyhydroxy acids and proteins and peptides. The preferred polymers are polyhydroxy acids such as polylactic acid, polyglycolic acid, and copolymers thereof.

Other microparticles

Other biocompatible particles such as virosomes or particles of polyamino acids, for example, poly-L-lysine could also be used. Similar methods for binding of heme to these materials would be used as is described below with reference to polymeric microparticles and liposomes.

Heme and Heme Derivatives

Metalloporphyrins are organic compounds whose structure includes a porphyrin ring which contains in its center a prosthetic metal atom, such as iron or magnesium, held by four inwardly-facing nitrogen atoms. Metalloporphyrins have been found associated with a variety of proteins such as globin, myoglobin and cytochromes, and in pigment molecules, such as chlorophylls. Such proteins consist of the metalloporphyrin moiety and the remaining portion of the protein called the apoprotein.

Heme, the common metalloporphyrin found in hemoglobin and cytochromes, is synthesized in animal cells by the chelation of an atom of iron with protoporphyrin IX using ferrochelatase. In hemoglobin, the heme molecule confers a reversible oxygen-binding capacity, whereas in cytochromes heme functions in electron transfer. Heme is a planar molecule and is capable of intercalating into double-stranded DNA (Aft, R. L. and Mueller, G. C., J. Biol. Chem. (1983), 258, 12069–12072, (1993); Carvlin, M. J. et al. *Nucleic Acids Res.* 11, 6121–6139 (1983)) and within lipid bilayers (Cannon, J. B., et al., *Biochem.* 23, 3715–3721 (1984); Tipping, E., et al., *Biochem. J.* 180, 327–337 (1979)). Heme contains two carboxyl groups which can serve as sites for peptide bond formation with amino group-containing molecules. Heme is readily available as an inexpensive reagent in the form of heme chloride (hemin, Sigma Chemical Co., St. Louis, Mo.).

The degradation of hemoglobin is an essential function of the liver and spleen as part of the removal of senescent erythrocytes from the circulation. The apoprotein in hemoglobin, i.e., globin, is degraded to its constituent amino acids, and heme is initially degraded by heme oxygenase to biliverdin. Biliverdin is then reduced further to bilirubin by biliverdin reductase. There appears to be some disagreement about the mechanism of binding and uptake of heme by the liver during its metabolism. Some evidence suggests that heme is transported to the liver complexed with carrier proteins such as hemopexin (Smith, A. and Morgan, W. T., *J. Biol. Chem.*, 259,12049–12053 (1984)), or albumin (Sinclair, P. R., et al., *Biochem. J.*, 256, 159–165 (1988)), while other data suggests that heme can bind directly to the hepatocyte membrane without the requirement for a carrier (Galbraith, R. A.,*J. Hepatol.*, 10, 305–310 (1990)). Whether or not a carrier protein is involved in the binding of heme to the hepatocyte, a heme receptor has been identified on the plasma membrane of hepatocytes (Galbraith, R. A., *J. Hepatol.*, 10, 305–310 (1990)) and other cell types (Galbraith, R. A., et al. *J. Biol Chem.*, 260, 12198–12202 (1985)), and this surface receptor binds heme specifically. The heme receptor is an integral membrane protein of apparent molecular weight 115 kilodaltons (kD) that may constitute up to 0.5% of the total liver membrane protein.

The nature of the protoporphyrin receptor(s) on the surface of cells is still unclear. A heme derivative that can be used instead of heme is an aminodiglyceride such as dioleoylphosphatidyl ethanolamine which contains a heme molecule attached to the ethanolamine residue, or other diglyceride with a heme group attached directly to the glycerol, as shown below:

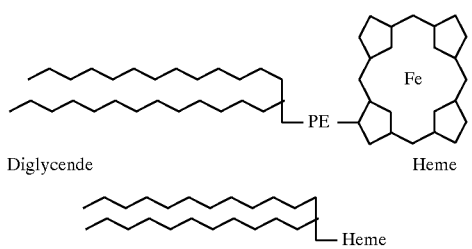

These lipids can be included directly during the formation of the liposomes.

Unless otherwise stated herein, heme and suitable heme derivatives are referred to jointly as "heme".

Methods for Incorporation of Heme

Heme can be bound to the microparticles either ionically or covalently, or intercalated into the phospholipid bilayer of the liposomes, most preferably covalently bound to avoid absorption to other proteins and removal from the liposome in vivo.

Binding to Polymeric Microparticles

Methods for covalently crosslinking heme to polymers are known. A heme molecule has two pendant carboxyl groups, two pendant alkene groups and four methyl groups. The carboxyl groups can be used to ionically or covalently link a polymer to the heme molecule. The alkene and methyl groups can form radicals, which can be used to covalently link a polymer to the heme molecule. To link the polymer to the heme molecule, the polymer needs to have at least one reactive group that reacts with a carboxyl group, an alkene group or a methyl radical to form an ionic or covalent bond. To crosslink the polymer and the heme molecule, the polymer must have at least two reactive groups.

Ionic Linkages: The carboxyl groups in a heme molecule can react in an acid-base reaction with amine groups on a polymer to form an ionic bond. The carboxyl groups can also be reacted with hydroxy groups on a polymer using a multi-valent ion, such as $Ca^{++}$ to effect the coupling.

Covalent Linkages: The carboxyl groups in a heme molecule can be reacted with pendant hydroxy, amine, thiol or carboxy groups on a polymer by means known to those skilled in the art of organic synthesis, for example, using a dehydrating agent such as DCC. The resulting products are esters, amides, thioesters and anhydrides, respectively. Representative methods are listed in Larock, "Comprehensive Organic Transformation", VCH, New York, 966–972 (1989), hereby incorporated by reference.

The pendant alkene groups in a heme molecule can be covalently coupled to a polymer containing alkene groups using a free-radical initiator. Alternatively, one can polymerize unsaturated monomers, such as acrylate monomers, in the presence of the heme molecule to form alternating copolymers incorporating the heme unit.

The pendant methyl groups form radicals when subjected to UV or gamma radiation. The methyl groups can be coupled to polymers containing pendant aliphatic carbon-hydrogen, carbon-chlorine or carbon-bromine bonds by subjecting the methyl groups on the heme molecule to UV or gamma radiation in the presence of the polymer.

Binding to Liposomes

To produce liposomes bearing heme covalently conjugated to their other surface, the lipid composition of the liposomes must include aminolipids or other compounds having a primary amino group available for covalent bonding to heme. Heme can be coupled to any molecule to be delivered to hepatocytes through appropriate chemical reactions. For example, phosphatidylethanolamine (PE) or dioleoyl PE present provides primary amino groups on the outer surface of the liposomes for conjugation with heme.

The covalent conjugation of heme to liposomes may be mediated by any reagent or method which promotes covalent peptide bond formation between carboxyl groups on heme and the primary amino group on the surface of the liposomes. For example, carbodiimide is well known as a reagent that promotes covalent conjugations and may be used to conjugate heme to primary amino groups on the outer surface of the liposomes, as described in R. R. C. New (ed.) (1992) Liposomes: a practical approach, pp. 179–180, IRL Press, Oxford, the teachings of which are incorporated herein. One of the benefits of using heme as a ligand is that each molecule contains only two carboxyl groups and no amino groups and thus, heme cannot couple to itself or in any way other than to primary amino groups contained on the outer surface of the lipid bilayer of a liposome.

The efficiency of coupling can be monitored using radio-labelled heme or by spectroscopy, using standard methodology, for example, as described by Galbraith et al., *J. Biol. Chem.*, 260, 12198–12202 (1985); Fuhrhop et al., In: *Porphyrins and Metalloporphyrins* (K. M. Smith, ed.), pp. 804–807 (Elsevier, Amsterdam 1975), incorporated herein by reference.

Hemin is known to intercalate into lipid bilayers and has been shown to spontaneously associate with liposomes. However, heme intercalated into a liposome can be very efficiently transferred from liposomes to heme binding proteins such as hemopexin present in the blood, which is not desirable and would decrease the efficacy of the delivery vehicle. Covalent attachment of heme to an aminolipid stabilizes the heme molecule on the outer surface of a liposome and may prevent its removal from the liposome once the heme-bearing liposome is injected into the bloodstream.

Compounds to be incorporated in Microparticles

A variety of drugs and compounds can be delivered to specific cells and organs using heme-bearing microparticles, including nucleic acid-based compounds, such as ribozymes and antisense oligonucleotides, proteins, carbohydrates, synthetic organic and inorganic molecules, monitoring agents, and combinations thereof, referred to herein as "therapeutic compounds" unless otherwise specified. In the preferred embodiment, the therapeutic compounds are nucleic acids, especially ribozymes, antisense oligonucleotides, aptamers, triplex molecules and antisense oligonucleotides. Examples of compounds falling within this group include DNA and RNA for transfection, and compounds to label intracellular molecules, as described, for example, by Felgner et al., *Proc. Natl. Acad. Sci. USA*, 84, 7413–7417; Lee et al., *Biochim. Biophys. Acta*, 1103, 185–197 (1992). Any therapeutic or function-enhancer could be incorporated, for instance, any liver enzyme for which there is a deficiency could be delivered using the heme system.

Methods of incorporation of compounds in microparticles.

In general, the compounds to be delivered are incorporated within the microparticles, either directly or via coupling to the heme. In the case of liposomes, the materials can be incorporated within or between the lipid bilayers, or bound to the outside of the liposomes, either ionically or covalently. In the case of the polymeric microparticles, the compounds can be dispersed throughout a solid polymeric microparticle (generally referred to as a microsphere) or incorporated within the core formed of a different material than the outer polymeric layer (generally referred to as a microcapsule), or bound to the outer surface of the polymeric microparticle. In the case where the compounds are bound to the surface of the microparticles, it may be preferable to bind the compound to be delivered to the microparticles at the same time as the heme.

Compound is preferably encapsulated within the microparticle when the compound is present during the preparation of the microparticles. This is relatively standard in terms of polymeric microparticles, where the compound is mixed into a polymer solution which is then formed into microparticles. In the case of liposomes, the material is incorporated during formation of the liposomes, for example, as described by Kim et al., 1983; Liu et al., 1992; Lee et al., 1992), in the resuspending buffer, or dried with the lipids.

Hydrophobic compounds or other compounds can be incorporated into the liposome between the lipid bilayers either by including the material during the formation of the liposome, that is, prior to the drying step, or by adding the material after the liposome has been formed and by relying on its spontaneous association based on the distribution of hydrophobicity within the molecule. One could also engineer a membrane-spanning peptide containing a hydrophobic region that could anchor other bound molecules to the inside or the outside of the bilayer.

Alteratively, cationic liposomes can be prepared by using mixtures including one or more lipids containing a cationic side group in a sufficient quantity such that the liposomes formed from the mixture possess a net positive charge which will ionically bind negatively charged compounds. Cationic liposomes have a great capacity for association with nucleic acids. Studies demonstrate that 4 $\mu$g lipid (dioleoyl trimethylammonium propane:dioleoyl phospatidylethanolamine 1:1 molar mixture) binds at least 1 $\mu$g DNA, and that this was 100% of the added dose, implying that this lipid was not saturated. This is representative of the binding stoichiometry of DNA to most postively charged lipids.

Examples of positively charged lipids that may be used to produce cationic liposomes include the aminolipid dioleoyl PE, which possesses a positively charged primary amino head group; phosphatidylcholines, which possess positively charged head groups which are not primary amines; and the recently designed N[1-(2,3-dioleyloxy)propyl]-N,N,N-triethylammonium ("DOTMA," described by Felgner, P. L. et al., *Proc. Natl. Acad. Sci USA*, 84, 7413–7417 (1987); Felgner, P. L. et al., *Nature*, 337, 387–388 (1989); Felgner, P. L., *Advanced Drug Delivery Reviews*, 5, 163–187 (1990)).

Cationic liposomes are particularly useful for delivering negatively charged compounds such as nucleic acid-based compounds, which bind ionically to the positively charged outer surface of these liposomes. Various cationic liposomes have previously been shown to be very effective at delivering nucleic acids or nucleic acid-protein complexes to cells both in vitro and in vivo, as reported by Felgner, P. L. et al., *Proc. Natl. Acad. Sci. USA*, 84, 7413–7417 (1987); Felgner, P. L., *Advanced Drug Delivery Reviews*, 5, 163–187 (1990); Clarenc, J. P. et al., *Anti-Cancer Drug Design*, 8, 81–94. Following association of the DNA with the preformed cationic liposome, it has been hypothesized that the membranes realign and form complexes entrapping the added nucleic acid possibly by fusion of adjacent liposomes.

The cationic liposomes can be conjugated or intercalated with heme, as described above, before, or preferably after incorporation of compound. For example, heme-bearing cationic liposomes can be mixed with a negatively charged drug or other compound, which will then complex with the surface of the liposomes ionically via positive charge-negative charge interactions.

Lipids other than primary amino lipids, that is, lipids with other functional groups to which a heme moiety can be attached through appropriate chemical reactions, can also be utilized as the means for attachment.

In an alternative method, oligonucleotide can be conjugated directly to the heme molecule or its derivatives for uptake into the hepatocytes of liver. The oligonucleotide could be a ribozyme, an antisense molecule, an aptamer or a triplex molecule. For example, following synthesis of an oligonucleotide, a C2 or C6 amino modifier can be coupled to the 5' end of the ribozyme. The oligonucleotide is deprotected in ammonia and purified by HPLC using standard protocols. Heme is attached to the 5' amino group of the ribozyme using carbodiimide as described in Example 1.

The ribozyme can be replaced with an antisense oligonucleotide or an aptamer or a triplex molecule for delivery into hepatocytes. Essentially, the same method can be used for conjugating a protein, a gene, a viral vector or any other therapeutic for delivery into liver. An example is the use of heme to deliver ara-AMP to liver to inhibit hepatotropic viruses like hepatitis B virus and hepatitis C virus. Ara-AMP is a nucleoside analogue that is inhibitory to HBV replication by interfering in the reverse transcription step in the life cycle of the virus. Other nucleoside analogues which are inhibitory to hepatotropic virus replication can also be introduced into infected liver cells after their chemical conjugation to heme.

Another method of conjugating heme to a nucleotide or protein is through a positively charged molecule like polylysine through a coupling reaction using a reagent such as carbodiimide or by ionic association. The ribozyme or other oligonucleotide is added to the heme-polylysine complex and incubated at room temperature for 15 min. to allow for the ribozyme to associate with the polylysine-complex. The RNA associates with polylysine primarily through ionic interactions due to the positive charge of the lysine moieties and the negative charge of the RNA.

Methods of treatment

The liposomes will preferably be administered systemically, most typically by intravenous or intraperitoneal administration, in an amount effective for delivery of the compound to the targeted cells. Other routes of administration that are useful include transdermal, transmucosal and enteral oral. Generally, the total amount of the liposome-associated compound administered to an individual will be less than the amount of the unassociated compound that must be administered for the same desired or intended effect. The effective amount is also dependent on whether the mode of administration is by a replicon, or vector-driven approach, e.g., a retroviral vector which amplifies the sequence it is carrying, or by a chemically-synthesized ribozyme approach.

The targeted disorders are any liver disease, but this methodology can be used to concentrate anything in the liver.

The present invention will be further understood by reference to the following non-limiting examples.

EXAMPLE 1

Preparation of heme-conjugated liposomes and measurement of binding of heme

Liposomes containing primary aminolipids were made using standard methods (Thierry, A. T., et al., *Cancer Comm.*, 1, 311–316 (1989)). Lipids were obtained either as powder or dissolved in chloroform from either Sigma Chemical Co. (St. Louis, Mo.) or from Avanti Polar Lipids, Aalabaster, Ala., and were stored desiccated at $-20°$ C.

In the initial experiment to determine the dependence of heme concentration on the conjugation of heme to the liposomes, the following standard liposomes were prepared.

468 μl (10 mg/ml) (6.9 μmoles) dimyristoyl phosphatidyl glycerol (DMPG), 260 μl (10 mg/ml) (12 μmoles) phosphatidyl ethanolamine (PE) and 172 μl (10 mg/ml) (5 μmoles) cholesterol were combined in a sterile glass test tube at room temperature, and the solvent was evaporated while vortexing in a vacuum desiccator at 55° C. to leave a film of dried mixed lipid. 10 μl phosphate buffered saline (PBS) was added to this film, and the tube was rotated to hydrate the film evenly. The hydrating film was left overnight. The liposomes were formed the following day by vortexing repeatedly with increasing additions of PBS. The liposomes were finally washed twice in 10 ml PBS, suspended in 400 μl PBS and stored at 4° C. prior to conjugation.

Heme was prepared by dissolving hemin to 20 mg/ml in 0.2N NaOH and rotating overnight at room temperature. This stock solution was stored for up to one week at 4° C. in the dark. For conjugation, the pH of the heme solution was brought down to approximately pH 7. Carbodiimide, the coupling agent, works best at acid pH, but heme starts to come out of solution below pH 7. Therefore, coupling was carried out at a pH as close to pH 7 as possible. 90 μl 1N HCl was added to 500 μl of 20 mg/ml hemin in 0.2N NaOH, and the final volume of this mixture was made up to 1 ml with distilled water to give a final heme concentration of 10 mg/ml.

500 μl conjugations were prepared in 1.5 ml EPPENDORF™ centrifuge tubes including 200 μl N-ethyl-N'-(3-dimethylaminopropyl) carbodiimide hydrochloride (EDC) (10 mg/ml), 100 μl liposomes and between zero and 200 μl heme (10 mg/ml, made up to 2200 μl with distilled water). The reactions were rotated in the dark overnight at room temperature. Each preparation was then washed three times with 1 ml 0.2N NaOH, each time centrifuging the liposomes at 14,000 rpm in an EPPENDORF™ centrifuge. The liposome pellet was finally taken up into 200 μl distilled water.

The amount of heme conjugated to the liposomes was determined spectroscopically using the method of Furhop, J. H. and Smith, K. M. In: *Porphyrins and metalloporphyrins* (K. M. Smith ed.), pp. 804–807 (Elsevier, Amsterdam 1975)). Briefly, the difference in absorbance of reduced heme and oxidized heme at 534 nm and 546 nm, respectively, gives a measure of the heme concentration in the sample when multiplied by an extinction coefficient. 100 μl of the liposomes were added to 700 μl distilled water and to this, 500 μl pyridine hemochrome (pyridine, 1N NaOH, water, 2:1:2) were added. This sample was divided into two parts and to one part a few granules of sodium dithionite were added and to the other part 10 μl of 1 mg/ml potassium ferricyanate were added. A spectrum was taken over the range 500 to 600 nm from these two samples and the concentration of heme present in the sample calculated.

The results are shown in FIG. 1 and demonstrate that, over the range of heme concentrations used, the amount of heme conjugated to the liposome increased with increasing heme in the coupling reaction. The efficiency of the reaction was quite low and decreased with high heme concentrations, indicating that coupling was saturable.

EXAMPLE 2

Effect of varying the level of PE in liposomes on the conjugation of heme

Liposomes were prepared exactly as above, but the amount of PE included in the mixture was varied from 0 μmoles to 12 μmoles. These preparations were diluted into 400 μl distilled water, and 100 μl was used in duplicate conjugation reactions as described above. The liposomes were washed three times as above and then suspended into 200 μl distilled water. Heme conjugated to a 100 μl sample of the liposomes was measured by the spectroscopic method described above.

Figure 2:
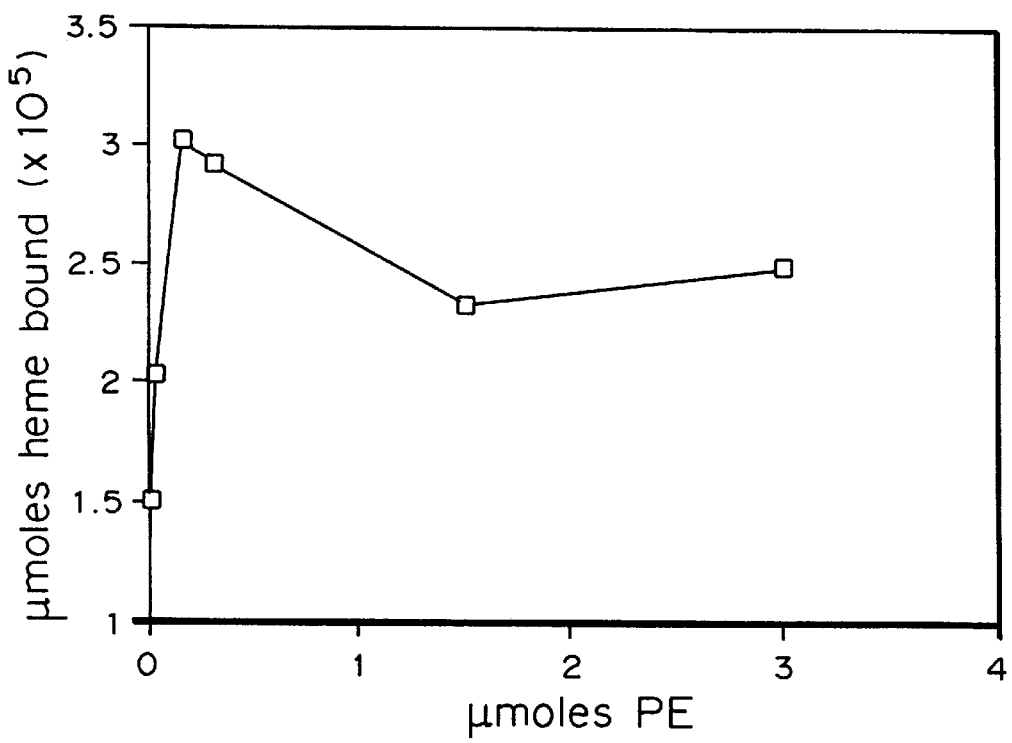
FIG. 2 is a graph of the effect of PE level on the conjugation of heme to DMPG/Ch/PE liposomes, measured as micromoles heme bound ($\times 10^5$) versus micromoles PE. The amount of heme was kept constant at 2 mg but the level of phosphatidylethanolamine used in the formation of the liposomes was varied between zero and three micromoles.

The results are shown in FIG. 2. Over the range of 0 to 0.6 μmoles of PE, the amount of heme bound to the liposomes was dependent on the amount of PE used in their formation, indicating that PE-dependent peptide bonding is probably occurring. 0.6 μmoles PE appeared to be the optimal level to give maximal coupling to the liposomes, since the amount of heme bound by the liposomes plateaued with PE levels above this amount.

However, when there was no PE included in the liposomes there was substantial binding of heme even after thorough washing to remove unbound heme. This indicates that heme can bind to liposomes without the necessity for the covalent coupling reagent carbodiimide. However, since heme is known to intercalate into lipid bilayers and, in this type of intercalative binding, may not orientate externally for recognition by heme receptors and because heme which is not covalently bound is removed from liposomes by heme-binding proteins in serum, heme-liposomes were prepared with carbodiimide for studies conducted to investigate the binding of heme-liposomes to cells in culture.

EXAMPLE 3

Binding of heme-liposomes to hepatocytes in cell culture

Two studies were conducted:

Experiment 1. DMPG:PE:cholesterol liposomes were prepared as above except that, instead of 10 μl distilled water, 10 μl of an [$\alpha$-$^{32}$P]dCTP-labelled oligonucleotide (approximately 100 ng) were used to rehydrate the dried lipid film. The radioactivity was used as a tag to follow the binding of liposomes to the cells. Unincorporated radioactivity was removed by washing the liposomes as described above. Heme was conjugated to the radioactively-tagged liposomes as described above, and the resulting heme-conjugated liposomes were finally taken up into 80 μl PBS. Control liposomes were prepared using the same preparation protocol but omitting the heme. 10 μl of each liposome were added in quadruplicate to HepG2 hepatocytes expressing hepatitis B virus surface antigen ("Acs cells", described by Sells, M. A., et al., *Proc. Natl. Acad. Sci. USA*, 84, 1005–1009 (1987)) in 2 ml binding buffer (PBS plus 100 mM glucose) in 6-well dishes. Acs cells were prepared by trypsinizing a stock plate, removing the cells, washing, and replating in the 6-well dishes at $1 \times 10^6$ cells per well. Cells were used three days after replating and were approximately 70% confluent. 100 μl of medium was removed from each well for a determination of the added radioactive counts. One set of dishes was incubated at 37° C. and another at 4° C. for three hrs. The cells were washed and were removed from the culture wells exactly as described by Galbraith et al., *J. Hepatol.*, 10, 305–310 (1990), and bound counts were determined using a Packard 3330 Liquid Scintillation Spectrometer.

Figure 3A:
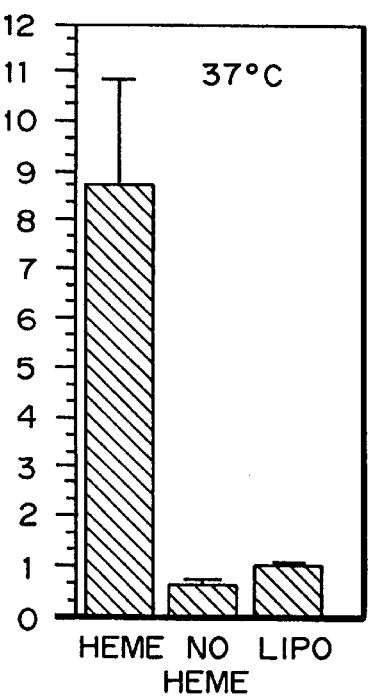
FIGS. 3A and 3B are graphs of percent liposomally-encapsulated radioactivity bound to or taken up by HepG2 cells by liposomes containing heme (FIG. 3A) and liposomes not containing heme (FIG. 3B) at either 37° C. or 4° C. A fixed amount (1 mg) of heme was used for conjugation.

This experiment was carried out at 4° C. and 37° C. to differentiate binding of liposomes to the cell surface from uptake, since cellular uptake at 4° C. is negligible. The results shown in FIGS. 3A (37° C.) and 3B (4° C.) demonstrate that heme-conjugated liposomes bind to and are taken up (see Heme columns) by hepatocytes to a significantly greater extent than control liposomes conjugated without heme (No Heme) or liposomes alone (Lipo.). In this experiment binding and uptake of Heme liposomes is greater than ten times more than controls, reaching an average of almost 9% of the added dose. These results indicate that conjugation of heme to liposomes can enhance liposome binding and uptake in this in vitro system.

Experiment 2. Labelled DMPG:PE:cholesterol liposomes were prepared as above and heme was conjugated to the liposomes in a reaction mixture that contained either 200 $\mu$l, 20 $\mu$l or 0 $\mu$l heme (10 mg/ml) as described above. The liposomes were diluted into 200 $\mu$l PBS for delivery to the cell cultures, and a small sample was taken for determination of heme binding as described in Example 1. Acs cells were prepared essentially as above, but $5\times10^5$ cells per well were dispensed into 6-well plates and left for three days before addition of liposomes. Prior to use, the cells were washed twice with 2 ml PBS and 2 ml Binding Buffer was returned to each well. 20 $\mu$l of each liposome preparation was pipetted into each well, mixed, and a 100 $\mu$l sample was taken for determination of Time 0 binding. One set of quadruplicate wells was placed at 37° C. and another set of duplicates was placed on ice for two hours. The liposomes were washed from the cells as described above in Experiment 1, and the cells were lysed after treatment with 1 ml Lysis Buffer (1M NaOH, 1% SDS) for 15 mins at room temperature (Galbraith, R. A. *J. Hepatol.,* 10, 305–310 (1990)). The cell lysate was transferred to a scintillation vial and 1 ml PBS was added to the culture wells to collect traces of the cell lysate. The samples were treated and counted as above.

Figure 3B:
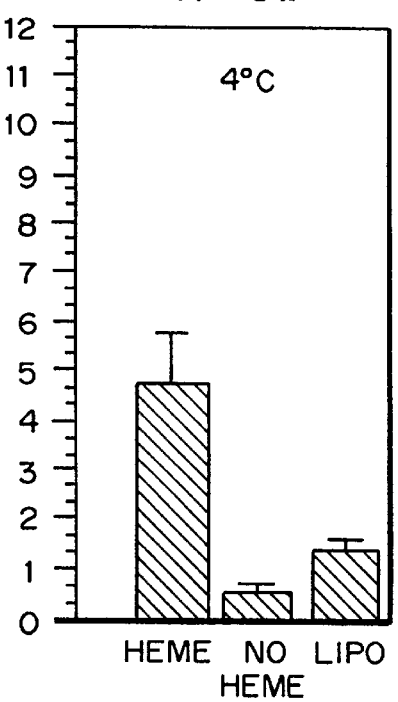
Figure 4A:
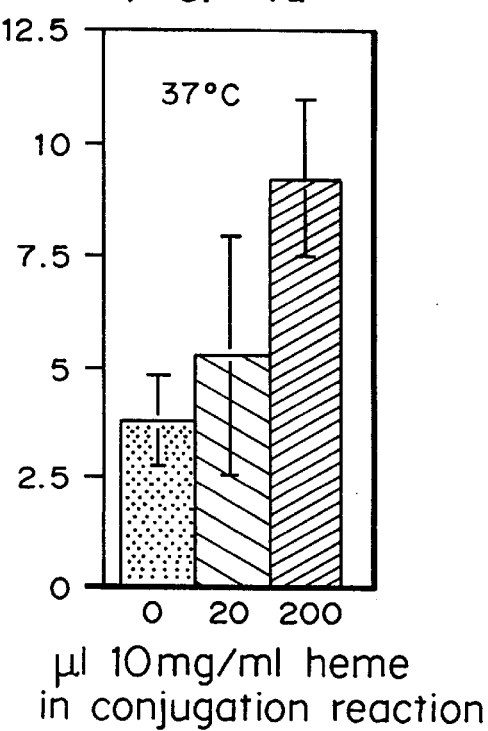
FIGS. 4A and 4B are graphs of percent radioactivity bound/taken up at either 37° C.
Figure 4B:
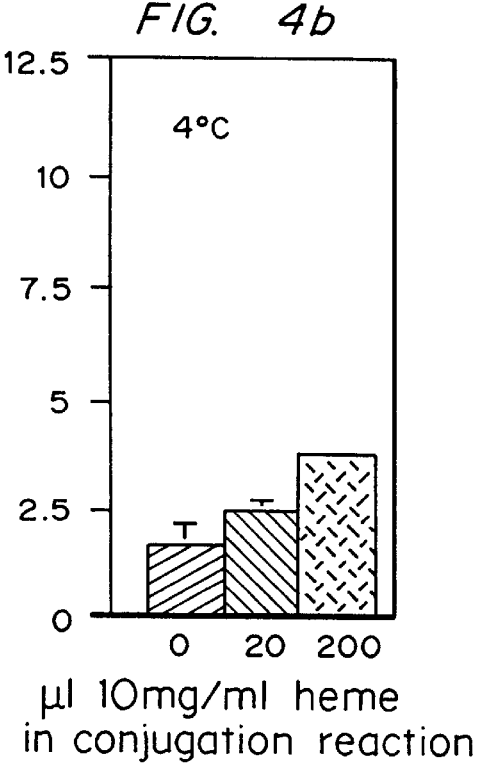

The results of this experiment are shown in FIGS. 4A and 4B. The results are similar to those shown in FIGS. 3A and 3B, but the difference in binding and uptake at 37° C. between the liposomes containing the greatest amount of heme and those containing no heme is less than in Experiment 1: an approximately ten percent increase compared with a 10 fold (1000%) increase.

The percentage of the heme-conjugated liposomes bound was approximately the same in both experiments, e.g., 9%. Also, in the second experiment, heme-conjugated liposomes promoted greater binding to hepatocytes than control liposomes at 4° C., in agreement with the previous data. There appears to be a stepwise increase in the amount of liposomes bound and taken up with increasing heme conjugated. The data from these experiments indicate that hepatocytes are targets for liposome delivery in vitro, possibly by a ligand-receptor mechanism that appears to be promoted by the presence of heme in or on the surface of the liposome. The difference in binding and uptake at 4° C. and at 37° C. between controls and heme-conjugated liposomes indicates the existence of a two step mechanism of liposome association, both of which are dependent on the presence of heme.

EXAMPLE 4

Direct conjugation of heme to an oligonucleotide

A ribozyme, an antisense molecule, an aptamer or a triplex molecule can be directly conjugated to a heme molecule or its derivatives for uptake into the hepatocytes of liver. As an example, a ribozyme directed against the epsilon region of the RNA of hepatitis B virus was synthesized on a DNA/RNA synthesizer (Applied Biosystems, Sunnyvale, Calif.) according to the manufacturers protocol. After the addition of the last nucleotide, a C2 or C6 amino modifier (Glen Research, Sterling, Va.) was coupled to the 5' end of the ribozyme. The oligonucleotide was deprotected in ammonia and purified by HPLC using standard protocols. Heme was attached to the 5' amino group of the ribozyme using carbodiimide as described in Example 1. The heme-ribozyme conjugate was purified by dialysis against several changes of water at 4° C. The purified heme-ribozyme complex was used for uptake into hepatocytes.

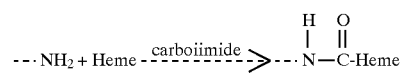

EXAMPLE 5

Conjugation of an oligonucleotide therapeutic to heme through polylysine

Another method of conjugating heme to a nucleotide or protein is through a positively charged molecule like polylysine. Polylysine is made up of sequential units of lysine moieties. A 10 mg/ml solution of polylysine in water (Sigma Chemical Co., St. Louis, Mo.) at pH 5.5 was mixed with an 0.5 mg/ml solution of heme (pH 5.5) and covalently coupled overnight at 4° C. using 10 mg/ml (final concentration) of carbodiimide. The conjugated material was dialyzed against water to remove excess heme. To a 0.1 ml of the heme-polylysine complex was added a solution of 100 $\mu$g of ribozyme in 0.1 ml $H_2O$ and incubated at room temperature for 15 min. to allow the ribozyme to associate with the polylysine-complex. The RNA associates with polylysine primarily through ionic interactions due to the positive charge of the lysine moieties and the negative charge of the RNA. The ribozyme-polylysine-heme complex was used for uptake into the hepatocytes as described in Example 1.

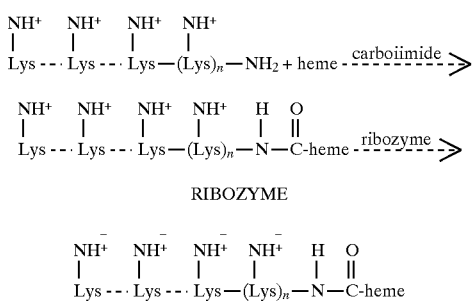

The method can be modified to deliver any therapeutic possessing a negative charge to hepatocytes. For example, the heme polylysine complex can be used to deliver an antisense molecule, an aptamer, a triplex molecule, a gene, a viral vector, a plasmid or any protein.

Modifications and variations of heme-bearing microparticles and methods of using such microparticles targeted delivery of compounds to cells expressing the heme receptor will be obvious to those skilled in the art from the foregoing detailed description. Such modifications and variations are intended to come within the scope of the appended claims.

We claim:

1. A method of targeting a liposome to a cell bearing a surface receptor for heme, comprising:
    chemically coupling heme to the surface of a liposome, and
    administering the resultant heme coupled liposome to a cell bearing a surface receptor for heme,
    thereby targeting a liposome to the cell.

2. The method of claim 1 further comprising associating a compound to be delivered to the cell with the liposome.

3. The method of claim 1 wherein the liposome comprises compounds having a primary amine available for binding and the heme is covalently bound to the liposome via the primary amine.

4. The method of claim 2 wherein the compound to be delivered is a nucleic acid.

5. The method of claim 4 wherein the compound is incorporated within the liposome.

6. The method of claim 4 wherein the compound is bound to the surface of the liposome.

7. The method of claim 6 wherein the liposome is a cationic liposome.

8. The method of claim 4 wherein the compound is bound to the heme which is bound to the liposome.

9. The method of claim 4 wherein the nucleic acid is selected from the group consisting of a ribozyme, an antisense nucleic acid, an aptamer, a triplex helix forming molecule, a gene, a viral vector, a plasmid, and a protein encoding sequence.

10. A method for delivering a compound associated with a liposome to a cell expressing a surface receptor for heme, comprising:

administering a liposome to a cell bearing a surface receptor for heme,
    wherein the liposome has
        (i) heme chemically coupled to its surface; and
        (ii) a compound to be delivered associated therewith;
    thereby delivering the compound associated with the liposome to the cell.

11. The method of claim 10 wherein the liposome comprises compounds having a primary amine available for binding and the heme is covalently bound to the liposome via the primary amine.

12. The method of claim 10 wherein the compound to be delivered is a nucleic acid.

13. The method of claim 12 wherein the nucleic acid is selected from the group consisting of a ribozyme, an antisense nucleic acid, an aptamer, a triplex helix forming molecule, a gene, a viral vector, a plasmid, and a protein encoding sequence.

14. The method of claim 12 wherein the compound is incorporated within the liposome.

15. The method of claim 12 wherein the compound is bound to the surface of the liposome.

16. The method of claim 15 wherein the liposome is a cationic liposome.

17. The method of claim 12 wherein the compound is bound to the heme which is bound to the liposome.

18. A liposome targeted to cells having a surface receptor for heme comprising heme covalently bound to the surface of the liposome.

19. The liposome of claim 18 further comprising a compound to be delivered to a cell having a surface receptor for heme.

20. The liposome of claim 17 wherein the compound to be delivered is a nucleic acid.

21. The liposome of claim 20 wherein the nucleic acid is selected from the group consisting of a ribozyme, an antisense nucleic acid, an aptamer, a triplex helix forming molecule, a gene, a viral vector, a plasmid, and a protein encoding sequence.

22. The liposome of claim 20 wherein the compound is incorporated within the liposome.

23. The liposome of claim 20 wherein the compound is bound to the surface of the liposome.

24. The liposome of claim 23 wherein the liposome is a cationic liposome.

25. The liposome of claim 20 wherein the compound is bound to the heme which is bound to the liposome.

26. The liposome of claim 18 wherein the liposome comprises compounds having a primary amine available for binding and the heme is covalently bound to the liposome via the primary amine.

* * * * *